United States Patent
Ash (10) Patent No.: US 7,998,101 B2
(45) Date of Patent: Aug. 16, 2011

(54) DEVICES AND METHODS FOR BODY FLUID FLOW CONTROL IN EXTRACORPOREAL FLUID TREATMENT

(75) Inventor: Stephen R. Ash, Lafayette, IN (US)

(73) Assignee: Renal Solutions, Inc., Warrendale, PA (US)

( * ) Notice: Subject to any disclaimer, the term of this patent is extended or adjusted under 35 U.S.C. 154(b) by 610 days.

(21) Appl. No.: 11/860,026

(22) Filed: Sep. 24, 2007

(65) Prior Publication Data

US 2008/0177216 A1    Jul. 24, 2008

Related U.S. Application Data

(62) Division of application No. 10/399,128, filed on Jul. 28, 2003, now Pat. No. 7,273,465.

(51) Int. Cl.
*A61M 37/00* (2006.01)
*C02F 1/00* (2006.01)
*F04B 49/00* (2006.01)
*C02F 1/44* (2006.01)

(52) U.S. Cl. ............ 604/6.11; 604/4.01; 604/5.01; 604/6.1; 210/739; 417/277; 417/475

(58) Field of Classification Search ............ 604/4.01, 604/5.01, 5.04, 6.09, 6.11, 65–67; 210/645, 210/646, 90, 739, 416.1; 417/118, 140, 477.1, 417/437, 277, 274, 275, 286, 297, 298, 475, 417/521, 477.12, 395

See application file for complete search history.

(56) References Cited

U.S. PATENT DOCUMENTS

| | | | |
|---|---|---|---|
| 2,495,711 A | 1/1950 | Fletcher |
| 3,520,298 A | 7/1970 | Lange |
| 3,545,438 A | 12/1970 | De Vries |
| 3,669,880 A | 6/1972 | Marantz et al. |
| 3,685,680 A | 8/1972 | Tenckhoff et al. |
| 3,850,835 A | 11/1974 | Marantz et al. |
| 3,888,250 A | 6/1975 | Hill |
| 3,939,069 A | 2/1976 | Granger et al. |
| 3,989,622 A | 11/1976 | Marantz et al. |
| 4,088,456 A | 5/1978 | Giorgi et al. |
| 4,116,589 A | 9/1978 | Rishton |
| 4,190,047 A | 2/1980 | Jacobsen et al. |

(Continued)

FOREIGN PATENT DOCUMENTS

EP    0 096 495    12/1983

(Continued)

OTHER PUBLICATIONS

Office Action in corresponding China application No. 2007101887559, filing date Oct. 12, 2001 from the State Intellectual Property Office, P.R. China (English translation included).

(Continued)

*Primary Examiner* — Leslie R Deak (74) *Attorney, Agent, or Firm* — Fish & Richardson P.C.

(57) ABSTRACT

Disclosed are devices and methods for the control of body fluid flow in the extracorporeal treatment of body fluid. Body fluid flow through on of a body fluid flow circuit 10, 50, 60 100, or 250 is controlled by alternatingly applying vacuum pressure and positive pressure to the circuit through a pumping chamber 30, 51, 66, 102, or 200 coordinated with flow control valves 40, 42, 44, 62, 114, 116, 118, and 120 to effect a net downstream flow of body fluid through the circuit.

9 Claims, 7 Drawing Sheets

U.S. PATENT DOCUMENTS

| | | | |
|---|---|---|---|
| 4,192,748 | A | 3/1980 | Hyden |
| 4,366,061 | A | 12/1982 | Papanek et al. |
| 4,412,917 | A | 11/1983 | Ajhopalo |
| 4,473,449 | A | 9/1984 | Michaels et al. |
| 4,474,853 | A | 10/1984 | Watanabe |
| 4,521,528 | A | 6/1985 | Kovach |
| 4,552,552 | A | 11/1985 | Polaschegg et al. |
| 4,662,829 | A | 5/1987 | Nehring |
| 4,680,122 | A | 7/1987 | Barone |
| 4,713,171 | A | 12/1987 | Polaschegg |
| 4,765,907 | A | 8/1988 | Scott |
| 4,911,703 | A | 3/1990 | Lysaght et al. |
| 5,004,459 | A | 4/1991 | Peabody et al. |
| 5,034,124 | A | 7/1991 | Kopf |
| 5,100,374 | A | 3/1992 | Kegeyama |
| 5,151,082 | A | 9/1992 | Gorsuch et al. |
| 5,173,125 | A | 12/1992 | Felding |
| 5,242,384 | A | 9/1993 | Robinson et al. |
| 5,300,017 | A | 4/1994 | Isoyama et al. |
| 5,498,338 | A | 3/1996 | Kruger et al. |
| 5,520,632 | A | 5/1996 | Leveen et al. |
| 5,549,674 | A | 8/1996 | Humes et al. |
| 5,595,909 | A | 1/1997 | Hu et al. |
| 5,641,405 | A | 6/1997 | Keshaviah et al. |
| 5,679,231 | A | 10/1997 | Alexander et al. |
| 5,712,154 | A | 1/1998 | Mullon et al. |
| 5,938,634 | A | 8/1999 | Packard |
| 5,944,684 | A | 8/1999 | Roberts et al. |
| 6,106,727 | A | 8/2000 | Krasnoff et al. |
| 6,419,462 | B1 | 7/2002 | Horie et al. |
| 6,899,693 | B2 | 5/2005 | Ghelli et al. |

FOREIGN PATENT DOCUMENTS

| | | |
|---|---|---|
| EP | 0 152 717 A1 | 8/1985 |
| EP | 0 659 444 A1 | 6/1995 |
| EP | 0659444 A1 | 6/1995 |
| EP | 0 745 396 A2 | 12/1996 |
| EP | 0 659 444 B1 | 5/1999 |
| FR | 2 585 251 | 1/1987 |
| JP | 57 188258 | 11/1982 |
| JP | 0 8187284 | 7/1996 |
| SU | 1 080 826 | 3/1984 |
| WO | WO 90/15631 | 12/1990 |
| WO | WO 00/18451 | 4/2000 |

OTHER PUBLICATIONS

Catapano et al., "Performance of the Dialytic Reactor with Product Inhibited Enzyme Reactions: A Model Study." *Bioseparation* 4 (3): 201-211 (1994).

Das et al., "Studies on Low-Cost Disposable Bioreactor for Bilirubin Detoxification," *Proceedings RC IEEE-EMBS #14th BMESI*, 1995, pp. 4.53-4.54.

Gordan, et al., "Augmentation of Efficiency by Continuous Flow Sorbent Regeneration Peritoneal Dialysis," *Trans. Amer. Soc. Artif. Int. Organs.*, XXII: 599-604 (1976).

Halligan, "The Human and Artificial Kidney," bit.listserv.transplant, Apr. 1, 1995, http://groups.google.com/groups?q=insubject:The+insubject:Human+insubject:and+insubject:Artificial+insubject:Kidney+author:Halligan&hl=en&lr=&ie=UTF-8&oe=UTF-8&as_drrb=b&as_mind=1&as_minm=4&as_miny=1995&as_maxd=5&as_maxm=4&as_maxy=1995&selm-Pine.3.89.9504010247.A16582-0100000%40pinyon.enet.net&rnum=1.

Kablitz et al., "Reciprocating Peritoneal Dialysis," *Dialysis & Transpl.* 7(3): 211-214 (1978).

Kablitz et al., "Technological Augmentation of Peritoneal Urea Clearance: Past, Present, and Future," *Dialysis & Transpl.*, 9 (8): 741-778 (1980).

Kang, "Efficacy of Lumbo-Peritoneal Versus Ventriculo-Peritoneal Shunting for Management of Chronic Hydrocephalus Following Aneurysmal Subarachnoid Hemorrhage," *Acta Neurochirurgica* 142 (1): 45-49 (2000).

Kolff et al., "A Membrane System to Remove Urea from the Dialyzing Fluid of the Artificial Kidney", Gulf South Research Inst. Report AK-2-7-2210, Mar. 15, 1978.

Mineshima et al., "Development of a Continuous Recirculating Peritoneal Dialysis Using a Double Lumen Catheter," *ASAIO J.*, 38 (3): M377-M381 (1992).

Lande et al., "In search of a 24 Hours Per Day Artificial Kidney," *J.Dialysis*, 1(8): 805-23 (1977).

Lewin et al., "Sorbent Based Regenerating Delivery System for Use in Peritoneal Dialysis," *Trans. Amer. Soc. Artif. Int. Organs* XX: 130-134 (1974).

Raja et al., "Recirculation Peritoneal Dialysis with Sorbent Redy Cartridge," *Kraftsow Renal Section and Womens' League for Medical Research Laboratories, Department of Medicine, Albert Einstein Medical Center*, Philadelphia, (Mar. 6, 1975, pp. 134-142).

Roberts, "The Regenerative Dialysis (REDY) Sorbent System," *Nephrology*, V4 (N4), 275-278 (1998).

Stephen, "Reciprocating Peritoneal Dialysis with a Subcutaneous Peritoneal Catheter," *Dialysis & Transpl.* 7(8) 834-838 (1978).

Stephen et al., "Combined Technological-Clinical Approach to Wearable Dialysis," *Int. Soc. Nephr.* Kidney Int. Supp. 8:S125-S132 (1978).

Stephen et al., "Recirculating Peritoneal Dialysis with Subcutaneous Catheter," *Trans. Amer. Soc. Artif. Int. Organs* XXII: 575-584 (1976).

Warden et al., "The Use of Reciprocating Peritoneal Dialysis with a Subcutaneous Peritoneal Catheter in End-Stage Renal Failure in Diabetes Mellitus," J. Surgical Res. 24: 495-500 (1978).

Webster, "Important Devices in Biomedical Engineering," Proceedings of the 1992 International Biomedical Engineering Days, 1992 IEEE, (Aug. 18-20, 1992), pp. 1-9.

"Blood Flow and Pressure Measurement," *IBM Technical Disclosure Bulletin*, Feb. 1971, pp. 2471-2472.

"Continuous Flow Dialyzer", *IBM Technical Disclosure Bulletin*, Jul. 1975, pp. 367-368.

Kellogg, "Centrifugal Artificial Kidney," *IBM Technical Disclosure Bulletin*, Apr. 1972, pp. 3433-3435.

European Search Report of European Patent Application No. 01981555.4-2310 dated Feb. 1, 2005, 5 pages.

DEVICES AND METHODS FOR BODY FLUID FLOW CONTROL IN EXTRACORPOREAL FLUID TREATMENT

CROSS-REFERENCE TO RELATED APPLICATION

This application claims priority to and is a division of U.S. patent application Ser. No. 10/399,128 filed Jul. 28, 2003 now U.S. Pat. No. 7,273,465. By this reference, the full disclosure, including the drawings, of said U.S. patent application is incorporated herein.

BACKGROUND

The present invention relates to devices and methods for the control of blood flow or the flow of other body fluids in the extracorporeal treatment of the blood or other fluid. More particularly, the invention relates to devices and methods for the control of blood flow or the flow of other body fluids in extracorporeal treatment through pumping the blood or other fluid with alternating positive and negative pressures applied to the blood flow circuit or body fluid flow circuit of a treatment apparatus. The invention also relates to devices and methods for the withdrawal of blood or other fluid from a patent by applying alternating positive and negative pressures to a fluid flow line.

Present extracorporeal blood treatment devices, such as hemodialysis, hemodialysis with a sorbent suspension, push-pull plasmapheresis, plasmafiltration, hemofiltration and liver dialysis machines, as well as machines for blood irradiation and phototherapy treatment, hyperthermia, hypothermia, blood gas management, etc., all have a common feature, in that they draw blood from a patient at as fast a rate as is practical, circulate the blood through a treatment unit, and then return the treated blood to the patient. This circulation of what amounts to essentially the whole blood supply of a patient outside the patient's body for treatment begins and ends with the passage of the blood through a single or dual lumen catheter system, generally assisted by a pump to increase the rate of blood flow, as well as to provide a regulated flow of blood throughout the treatment. Previous systems most typically use roller pumps set to a specified rate, which is carefully monitored and controlled by an attending nurse or physician, or by the user in home use dialyzers.

Other treatment protocols, as for example, peritoneal dialysis, also involve the withdrawal of fluid from a patient in large volumes for disposal or for treatment by the action of an extracorporeal treatment device. Such other treatments, likewise, depend on the efficient drawing of a fluid from the patient without causing injury, and in some cases, circulating the fluid through a treatment unit, and returning the treated fluid to the patient.

A significant problem that often arises in extracorporeal blood treatments is venous collapse. The risk of collapse necessitates the careful monitoring of the blood pump by trained personnel. If the blood flow from the patient slows to below the rate at which the blood pump is operating, vacuum pressure builds in the patient access line. If this vacuum is too great, the vein around the catheter can collapse, stopping the blood flow. Continued pump action on the collapsed vein can cause damage to the veins, excessive bruising, and may require the catheter to be relocated to a new vein. Excessive vacuum pressures can also cause blood clotting in the dialyzer or other treatment unit, as well as hemolysis. For this reason, blood treatments are usually started at a sub-optimum blood flow rate, which is then slowly increased as the patient's veins will allow. The required monitoring places additional burdens on attending nurses and physicians, as well as increased risks on the patients. The skill level and attention required in monitoring also limits the use of in-home treatment systems operable by the patients themselves.

A similar risk in the withdrawal of other fluids from the body, is the collapse of tissue surrounding the catheter, blocking the flow of the body fluid into the catheter and potentially causing bruising or other tissue damage.

It is evident there remains a need for improved devices and methods for withdrawal and extracorporeal treatment of blood or other body fluids, particularly for control devices that reduce the risk of venous collapse and tissue collapse, while maximizing the flow rate of blood or other fluid for any given patient, thereby minimizing the burden of monitoring the flow.

SUMMARY OF THE INVENTION

The present invention relates to systems, devices and methods for extracorporeal treatment of body fluids. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one aspect of the present invention, there is provided an extracorporeal blood treatment device comprising a blood treatment unit having a blood flow circuit therethrough with a blood inflow line and a blood outflow line, the flow lines originate and end at a patient access, such as for example, a single or dual lumen catheter set; a pumping chamber coupled to and in fluid communication with the blood flow circuit and configured to alternately draw blood into the chamber at a predetermined vacuum pressure and push blood out of the chamber at a predetermined positive pressure; and at least one flow control valve in fluid communication with said blood flow circuit configured to effect a net downstream flow through the blood flow circuit.

In various embodiments of the invention, the blood treatment unit is, for example, but without limitation, a hemodialysis device, a hemodialysis with a sorbent suspension device, a push-pull plasmapheresis device, a plasmafiltration device, a hemofiltration device, a liver dialysis device, a blood irradiation or phototherapy device, a blood gas management device, or a hyper/hypothermia treatment device.

In one form, the present invention provides a pumping chamber that comprises a flexible, fluid impermeable membrane (or a bag serving the same function), whose interior is in fluid communication with said blood flow circuit. The membrane is positioned within an outer chamber coupled to a source of vacuum pressure and a source of positive pressure, such that the membrane expands when vacuum pressure is drawn on the outer chamber, thereby communicating the vacuum pressure to the blood flow circuit, and such that the membrane is compressed when positive pressure is applied to the outer chamber, thereby communicating the positive pressure to the blood flow circuit. Thus, by controlling the one or more valves and applying a predetermined vacuum pressure or a predetermined positive pressure within the outer chamber, blood is caused to enter or exit the pumping chamber, respectively, in a controlled manner to achieve flow through the circuit.

In another form, the present invention provides a body fluid pumping assembly for a fluid flow circuit. The assembly comprises: a first chamber including a first expandable membrane therein and defining first inner chamber; a first body fluid inlet into the first inner chamber providing fluid communication with the fluid flow circuit; and a first gaseous port into the first chamber. The assembly further comprises: a first sensor providing a first signal representative of the body fluid flow rate in the blood flow circuit; and a control device responsive to the first signal and adapted to control blood flow into the first inner chamber.

In another form, the present invention provides an extracorporeal body fluid treatment device. The extracorporeal device comprises: a body fluid treatment unit having a body fluid flow circuit therethrough including a body fluid inflow line and a body fluid outflow line; a pumping assembly comprising a first pumping chamber in communication with said body fluid flow circuit and configured to alternately draw body fluid in under a predetermined vacuum pressure and push body fluid out under a predetermined positive pressure; a sensor for detecting the body fluid flow rate in the body fluid flow circuit; and means for effecting the first pumping chamber to alternately draw body fluid in and push body fluid out.

In still yet another form, the present invention provides a method for providing a flow of a body fluid through a fluid flow circuit for extracorporeal treatment of the body fluid. The method uses a pumping assembly that comprises a first pumping chamber having a first predetermined interior volume and in fluid communication with the fluid flow circuit. The method comprises: withdrawing body fluid from an animal under a pre-selected vacuum pressure into the first pumping chamber to provide said chamber with a desired first amount of body fluid: detecting a first flow rate of the body fluid; and controlling the flow of body fluid in the fluid flow circuit in accordance with the first flow rate of the body fluid.

In a preferred embodiment, the pump is fluidly coupled to the blood flow circuit on the blood inflow line, i.e., prior to the treatment unit. In another preferred embodiment, the predetermined vacuum pressure is no less than about −300 mm/Hg and the predetermined positive pressure is no greater than about 300 mm/Hg. In another preferred embodiment, the predetermined vacuum pressure is between about −250 and about −150 mm/Hg and the predetermined positive pressure is between about 150 and about 250 mm/Hg. In another preferred embodiment, the vacuum pressure is about −250 and the positive pressure is about 250 mm/Hg.

It is one object of the present invention to provide a body fluid pumping device and method for using the pumping device.

Further objects, features, aspects, forms, advantages and benefits shall become apparent from the description and drawings contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

In general the present invention comprises a pumping assembly for effecting fluid flow through a fluid flow circuit, for which pumping assembly is particularly advantageous for use in a extracorporeal fluid treatment system. The pumping assembly includes a pumping chamber coupled to and in fluid communication with the fluid flow circuit and configured to alternately draw body fluid into the chamber under a predetermined vacuum pressure and push the body fluid out of the chamber under a predetermined positive pressure.

Figure 1:
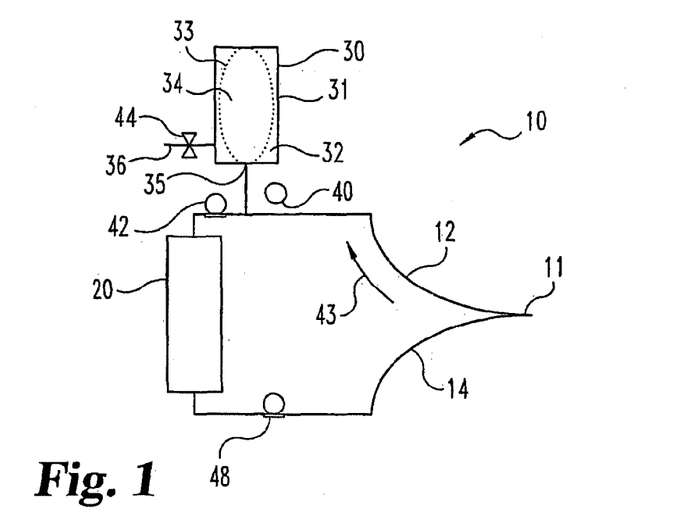
FIG. 1 is a schematic illustrating one embodiment of a body fluid pumping assembly depicted during the fluid inflow portion of the pump cycle according to the present invention.

FIG. 1 is a schematic drawing illustrating the relationship between selected elements of one embodiment of the present invention. An extracorporeal body fluid flow circuit 10 is defined at least by patient access 11, body fluid inflow line 12, pumping chamber 30, body fluid treatment unit 20, body fluid outflow line 14, and returning to patient access 11. Patient access 11 is depicted as a single lumen catheter set. However it is understood that the patient access may be any type of fluid access known in the art including, but not limited to, a single lumen or dual lumen catheter sets, inserted as appropriate for the body fluid being treated, the specific treatment being administered, and the physician's preference.

Pumping chamber 30 comprises an outer housing 31 defining chamber 32 and a flexible membrane 33 defining inner chamber 34. Outer housing 31 is substantially rigid or non-deformable and includes at least one gaseous inlet 36 into chamber 32. Outer housing 31 is sealed—except for inlet 36—to maintain either reduced or negative pressure (vacuum) and a positive pressure in chamber 32. Inlet 36 allows passage of gas, typically air, or if desired an inert gas or fluid, into and out of chamber 32 to provide the negative or positive pressure as desired. The pressure, either positive or negative, in chamber 32 exerts a force on the flexible membrane 33. Flexible membrane is capable of being expanded and siphoning or withdrawing body fluid from the patent through access 11 and inflow line 12.

The interior volume of housing 31 and consequently chamber 32 can be a desired volume. In preferred embodiments, interior volume of chamber 32 is at least 5 ml, more preferable at least 10 ml, and still more preferably at least 20 ml. Housing is constructed to withstand a wide range of pressures including positive and negative pressures of at least ±300 mm/Hg Hg and more preferably at least ±500 mm/Hg.

Membrane 33 is a flexible partition that defines inner chamber 34. Preferably membrane 33 is provided as flat membrane or balloon structure. Although it will be understood that the present invention includes within its scope flexible membrane having other configurations, for example as a diaphragm or tubular structure partitioning housing 31 into one or more sections. Membrane 33 includes at least one fluid port or inlet 35 providing fluid communication with circuit 10. In other embodiments membrane 33 can include two or more ports or inlets to provide different entrance and exit ports for the body fluid to flow into and out of inner chamber 34. Membrane 33 can be provided to define any desired internal volume, when fully expanded. Preferable membrane is provided to define an inner chamber that corresponds to or approximates the interior volume of housing 31.

Membrane 33 is provided to be a flexible material that readily deforms under an imposed positive or negative pressure. Preferably membrane 33 exhibits little resistance to expansion and/or contraction. This provides distinct advantages by minimizing any additional pressure conducted to any fluid inside chamber 34, flow circuit 10 (and the patent's veins) other than the pressure applied to chamber 32. Membrane 31 can be, but is not required to be, an expandable or elastic material. In other embodiments membrane is a substantially non-expandable material that is inflated or deflated depending upon the applied external pressure without substantially increasing or increasing its exterior surface area.

Circuit 10 includes at least one more preferably two or more valves 40 and 42 controlling body fluid flow into inner chamber 34 and optionally in circuit 10. In the illustrated embodiment, first valve 40 is positioned upstream pumping chamber 30 and second valve 42 is positioned downstream chamber 30 in circuit 10. Additionally, valves can be formed integral with one or more inlets into the pumping chamber. For example one or both of fluid inlet 35 and gaseous inlet 36 can include an integral valve controlling the flow of either body fluid or gases into and out of chamber 32. Valves for use in this invention can be selected from a type of valve commonly used in the medical arts. The valves can be flow direction control valves capable of directing fluid flow through a selected one of two or more lines or circuits. Alternative, the valves can be check valves permitting fluid flow through the valve in one direction only. In still yet other embodiments, the valves can be variable flow valves capable of varying the flow rate of the fluid through one or more lines or circuits. In still yet other embodiments, a combination of different valve-types can be included in the present invention.

Preferably one or more of the valves in the fluid flow circuit are coordinated with the pumping chamber to effect a net downstream flow through the blood flow circuit. FIG. 1 illustrates the vacuum phase of a pumping cycle. In that pumping cycle first valve 40 is open providing fluid communication from inflow line 12 and into inner chamber 34. In a preferred embodiment, opening of first valve 40 is coupled with evacuation of chamber 32. Evacuation of chamber 32 can be effected connecting inlet 36 to a vacuum source and/or by opening third valve 44 already connected to a source of vacuum. Optionally second valve 42 is closed to prevent back flush of any fluid downstream of chamber 32. In a more preferred embodiment, second valve 42 is coupled to one or more of opening of first valve 40, evacuation of chamber 32 and opening of third valve 44.

Chamber 32 is evacuated to a first pre-selected pressure. Preferably the first pre-selected pressure is selected considering one or more conditions, such as, ensuring patent safety, reduce potential for collapsing a vein, inducing blockages in one or more lines, chambers or treatment units, optimizing blood flow, minimizing the time period to complete one cycle, optimizing treatment period for the body fluid and/or pressure for treatment of the body fluid. In a more preferred embodiment the first pre-selected pressure is selected to be greater (more positive) than about −400 mm/Hg Hg, more preferably greater than about −300 mm/Hg, and still more preferably between about −300 and about −200 mm/Hg.

The low first pre-selected pressure in chamber 32 exerts a force on membrane 33. Membrane 33 deforms from a contracted or closed state to an enlarged or expanded state. This, in turn, withdraws body fluid from circuit 10, preferably through inflow line 12, access 11 and from a patent's vein (not shown).

Body fluid continues to flow into inner chamber 34 as indicated by arrow 43 until one or more conditions occur. Membrane 33 can expand until the inner chamber 34 substantially equals or fills chamber 32, one or more of valves 40 and 36 close, or the gas flows back into chamber 32. One or more of these conditions can be controlled either manually, automatically, or by a controller, such as a microprocessor, coupled to a detector generating signals indicative of the conditions of one or more of the units combined with the flow circuit. Once body fluid ceases to flow into inner chamber 34, the body fluid can be retained inside inner chamber 34 as desired or more preferably expelled from inner chamber 34 and forced along the flow circuit. Control of the cycling of the pump chamber and one or more operably coupled valves is discussed below in more detail.

Figure 2:
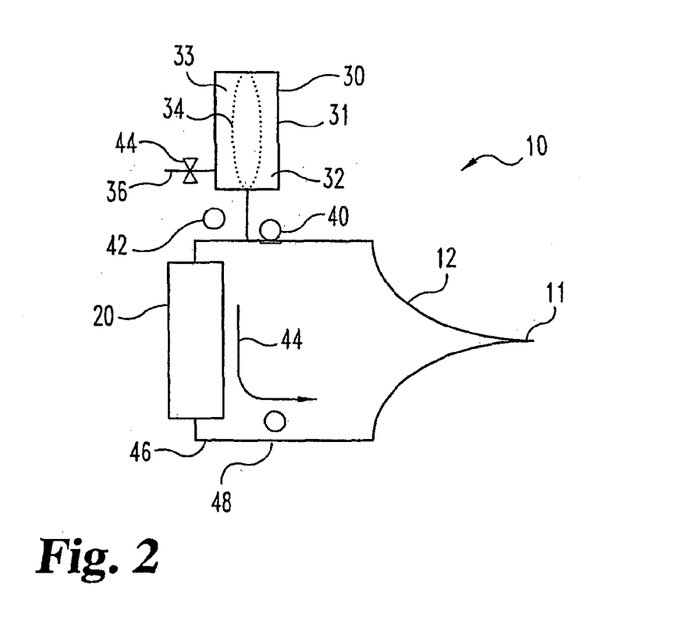
FIG. 2 is a schematic illustrating the body fluid pumping assembly of FIG. 1 depicted during the fluid outflow portion of the pump cycle according to the present invention.

FIG. 2 is a schematic illustrating one embodiment of a positive pressure phase of the pumping cycle for circuit 10. Inlet 36 is connected to a pressure source. For example, third valve 44 can be a flow-directing valve capable of directing either a vacuum source or a pressure source to inlet 36. Gas or other pressuring medium flows into chamber 32 and increases the pressure from a first pre-selected pressure to a second pre-selected pressure. The second pre-selected pressure is higher than the first pre-selected pressure. Consequently the positive pressure exerts force on the expanded membrane 34 forcing the expanded membrane to contract or collapse and expelling the contained body fluid out into flow circuit 10. Preferably in the positive pressure cycle first valve 40 closes or otherwise inhibits body fluid from flowing to or from inflow line 12 and into inner chamber 34. Opening valve 42 permits fluid communication between a downstream portion 46 of fluid circuit 10. The body fluid expelled from inner chamber 34 flows through open valve 42 and into circuit portion 46.

Thus, the cycle volume of body fluid in inner membrane 34 is expelled downstream, as generally indicated by arrow 45, through treatment unit 20, and prevented from back flushing through inflow line 12 to patient access 11. Optional control valve 48 is open to allow re-infusion of body fluid into the patient through patient access 11.

For blood treatments, catheters may be inserted into the veins or arteries of the patient directly, or into a fistula or other grafted access as indicated by the treatment to be given.

Body fluid treatment unit 20 may be any extracorporeal body fluid treatment device known in the art which treats a body fluid as it is circulated out from a patient, through the treatment device and back into the patient. Suitable treatment devices include, but are not limited to devices for peritoneal dialysis, hemodialysis, hemodialysis with a sorbent suspension, push-pull plasmapheresis, plasmafiltration, hemofiltration, liver dialysis, blood irradiation or phototherapy, blood gas management, or hyperthermia or hypothermia treatment. Such devices are known in the art and include, for example, those described in U.S. Pat. No. 4,661,246 (dialysis of body fluids); U.S. Pat. Nos. 5,277,820, 5,536,412 and 5,919,369 (hemofiltration and plasmafiltration); U.S. Pat. Nos. 5,354,277 and 5,476,444 and U.S. patent application Ser. Nos. 09/126,372 and 09/235,449 (hyperthermia treatment); and U.S. patent application Ser. No. 09/284,904 and International Application No. PCT/US97/19489, Publication No. WO 98/17333, Publication Date: 30 Apr. 1998 (peritoneal dialysis), each of which is incorporated herein by reference in its entirety.

Figure 3:
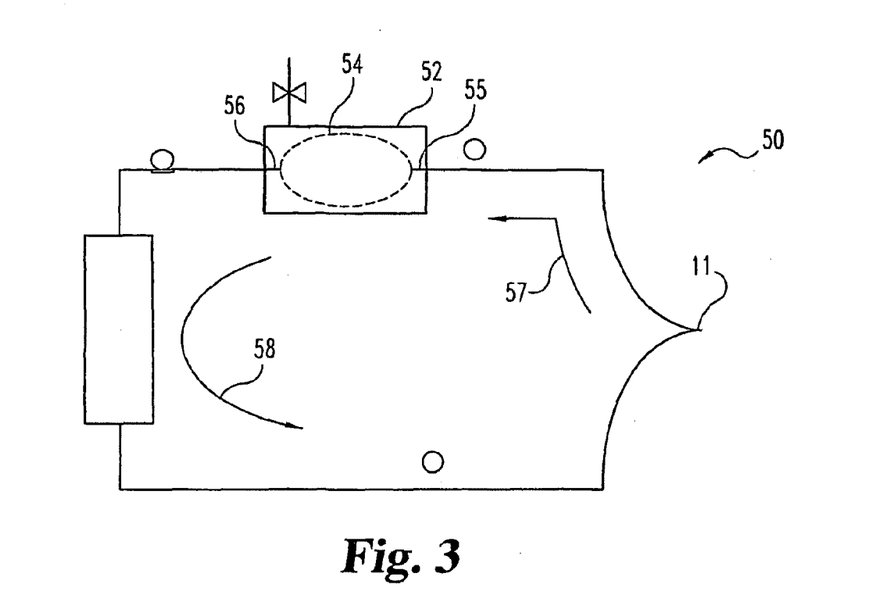
FIG. 3 is a schematic illustrating one embodiment of a body fluid pumping assembly having a fluid inlet, a fluid outlet, and two flow control valves depicted during an inflow portion of the pumping cycle according to the present invention.
Figure 4:
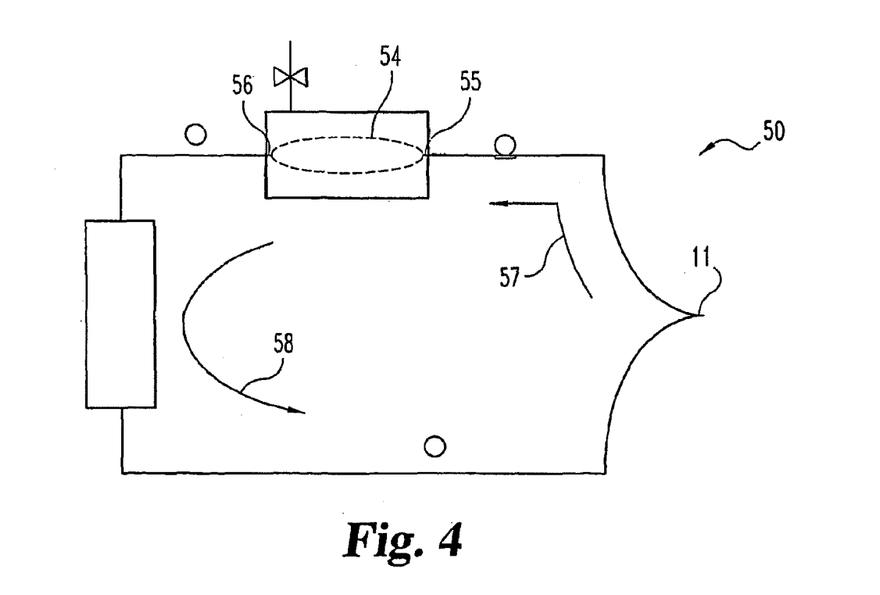
FIG. 4 is a schematic illustrating the body fluid pumping assembly of FIG. 3 depicted during an outflow portion of the pumping cycle according to the present invention.

FIGS. 3 and 4 are schematic illustration of a flow circuit 50 having a pumping chamber with separate inlet and outlets for effecting the flow of a body fluid. Flow circuit is formed similarly to circuit 10 and the same reference numbers are used to denote same components. FIG. 3 illustrates flow circuit 50 while pumping chamber 57 is in the vacuum or withdrawing portion of the pumping cycle. FIG. 4 illustrates the flow circuit 50 while pumping chamber 54 is in the pressurization or expelling portion of the pumping cycle.

Pumping chamber 50 is coupled in-line along the body fluid inflow line. Pumping chamber 51 has an outer chamber 52 and inner membrane 54 similar to the chamber described above, but has separate inflow and outflow ports 55 and 56, respectively, in the inner membrane 54 and outer chamber 52, as compared to a single port for both inflow and outflow. This withdraws fluid from a patient through access 11 as indicated by arrow 57, and subsequently pushes the withdrawn fluid through circuit 50 in the direction indicated by arrow 58.

Figure 5:
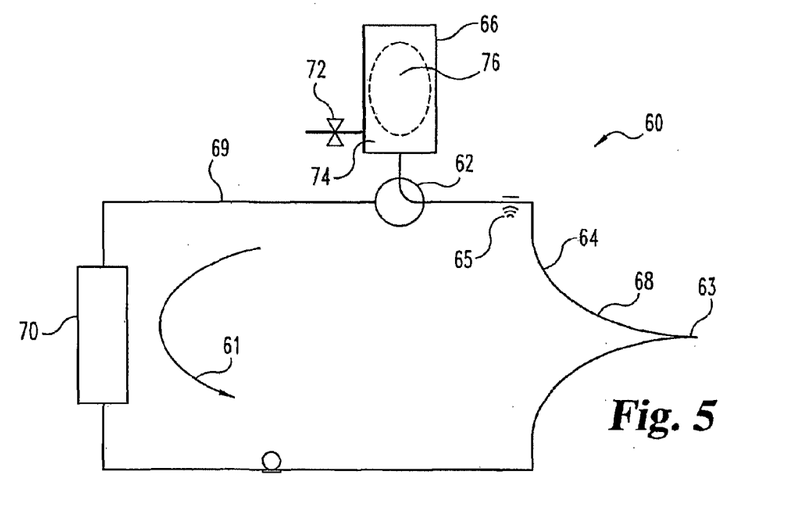
FIG. 5 is a schematic illustrating one embodiment of a blood pumping assembly having a fluid flow directing valve in combination with a blood treatment system depicted during an inflow portion of the pumping cycle according to the present invention.
Figure 6:
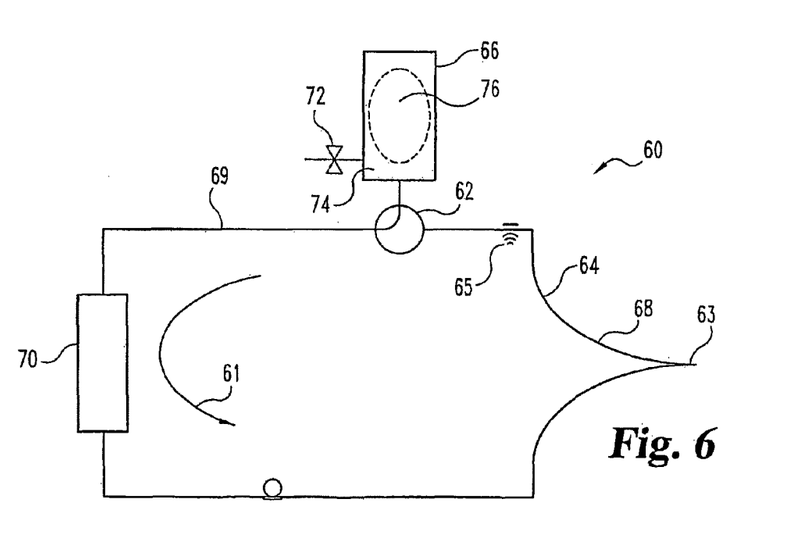
FIG. 6 is a schematic illustrating the blood pumping assembly of FIG. 5 depicted during an outflow portion of the pumping cycle.

FIGS. 5 and 6 are schematic illustrations of fluid pumping system 60 having at least flow directional valve 62 directing fluid flow in circuit 64. In the illustrated system fluid flows in circuit 64 in a counter-clockwise direction depicted by arrow 61, starting from patent access 63 through inflow line 68, assisted by pumping chamber 66 through outflow line 69 to treatment unit 70 and eventually back to patent access 63. System 60 also includes at least one fluid flow sensor 65 for detecting the flow rate of a body fluid in circuit 64.

Referring specifically to FIG. 5, which depicts the vacuum pressure phase of a pumping cycle, flow directional valve 62 is positioned between pumping chamber 66 and flow circuit 64. Valve 62 is shown in a first position and that to direct fluid flow from inflow line 68 into pumping chamber 66. Preferably flow directional valve 62 is operably coupled to valve 72 controlling gas flow into and out of outer chamber 74. In a more preferred form, valve 62 is operably coupled with gas valve 72 via a control unit (not shown) whereby when gas valve 72 opens to a vacuum source to withdraw the gas from outer chamber 74, flow directional valve 62 simultaneously switches to a first position directing fluid flow into body fluid chamber 76.

Referring specifically to FIG. 6, which depicts the positive pressure portion of the pumping cycle, flow directional valve 62 now directs fluid flow out of body fluid chamber 76 and through outflow line 69 to treatment unit 70. In a preferred form, when gas valve 72 opens to pressure chamber 74, flow control valve 62 switches from a first position directing fluid flow into body fluid chamber 76 to a second position directing the fluid received within body fluid chamber 76 to outflow line 69.

As mentioned above, in this embodiment, flow directional valve 62 is operably coupled with the vacuum and positive pressure source switching by gas valve 72. When vacuum pressure is switched to positive pressure to expel the body fluid from the body fluid chamber 76, the flow directional valve 62 switches from a first position to a second position directing the flow of fluid flow downstream toward the treatment unit 70 and eventually out to the patent through access 63.

In an alternative embodiment, that is particularly useful when body fluid treatment unit 70 includes a filtration or dialysis treatment, a portion of the vacuum pressure may be diverted to draw a portion of body fluid in the treatment unit 70 back upstream toward and/or into body fluid chamber 76 by leaving control valve 40 at least partially open (for the embodiment depicted in FIG. 1) or by orienting switching valve 62 (for the embodiment depicted in FIG. 4) such that inlet line 68 fluidly communicates with treatment unit 70 during at least a portion of the cycle phase wherein vacuum pressure is exerted in the pumping chamber. This provides a condition referred to as back washing that advantageously remixes the body fluid being treated to avoid phase separations or settling of the fluid. Furthermore, in a filtration or dialysis treatment, filtration/dialysis membranes tend to become clogged by fluid-borne components on the body fluid side of the membrane, and/or sorbent particles, if present in suspension, on the dialysate side of the membrane. The transmittance of vacuum pressure downstream, back-flushing the fluid, draws fluid across the membrane from the dialysate or sorbent side of the membrane, thus washing deposited, clogging, fluid components off the membrane. Drawing fluid back across the membrane also balances the fluid lost during the dialysis or filtration, reducing the need for fluid replacement to the patient.

Figure 7:
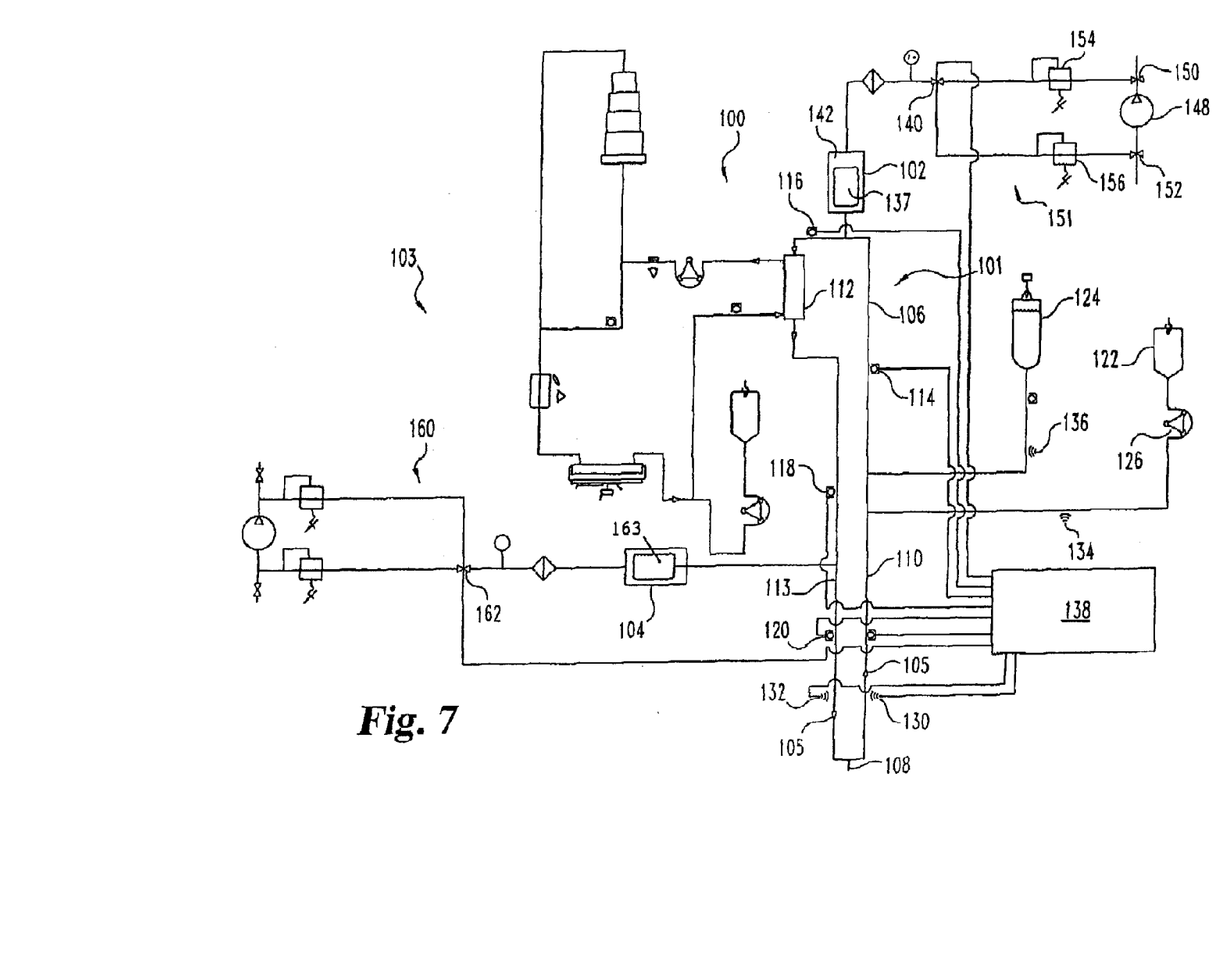
FIG. 7 is a schematic illustrating one embodiment of a body fluid treatment system including a two pumping chambers according to the present invention.

FIG. 7 is a schematic illustration of a dialysis treatment system 100 provided according to this invention. Treatment system 100 includes body fluid side or circuit 101 and a dialysate or sorbent side 103: both circuits flowing into a fluid treatment unit 112 such as a hollow fiber dialyzer. Body fluid circuit 101 includes two pumping chambers, 102 and 104 effecting fluid flow through fluid circuit 106 in a counter-clockwise direction depicted by arrows 105. Fluid circuit 106 includes a single lumen patent access 108, inflow line 110, body fluid treatment unit 112 a fluid outflow line 113 and terminating again at patent access 108. A plurality of valves and fluid flow sensors are positioned along fluid circuit 106. First pumping chamber 102 is positioned between first valve 114 and second valve 116. Similarly second pumping chamber 104 is positioned between third valve 118 and fourth valve 120. Further the combination of first pumping chamber associated valves 114 and 116 are located upstream of fluid treatment unit 112 while the combination of the second pumping chamber 104 and associated valves 116 and 120 are located downstream of fluid treatment unit 112.

Additional fluid lines connecting other sources of fluid such as anticoagulant solution source 122 and a priming/rinsing solution source 124, are connected to inflow line 110. The additional lines can include separate pumps such as roller pump 226 or use gravity feed under the control of one or more valves and optionally with sensing devices to monitor the amount of fluids infused into inflow line 110.

Flow sensors may optionally be placed along any or all flow lines shown as sensors 130, 132, 134, and 136. Flow sensors may be selected from any type of detector known in the art. provided sterile conditions are maintainable, if necessary, and that the detector is compatible with the body fluid being treated. Such detectors may include optical detectors, ultrasonic and trans-sonic detectors. One preferred ultra sonic detector particularly suited for applications when the body fluid is blood, is a transit time ultrasonic flow meter sold by Transonics, Inc.

The sensors provide a signal indicative of the flow rate of the fluid in the line. Typically the flow rate is measured in terms of ml per minute. The signal can be visual detected on an output device such as a visual readout, gage, dial, lighted display or liquid crystal display, or maintained in a electronic memory device and the like. Additionally the signal can be provided to one or more controllers for controlling other elements in the flow circuit such as valves, pump pressure, and audible warning devices.

In one preferred embodiment of the invention, ultrasonic flow detector 130 or an equivalent sensor or sensors, detect flow rates or changes in flow rates in flow circuit 110 and into and out of pumping chamber 102. During the vacuum phase of a pump cycle, body fluid flow is detected by sensor 130 flowing into body fluid chamber 137 of pumping chamber 102. When the flow rate, which flows under constant vacuum pressure, slows due to greater resistance as body fluid chamber 137 reaches capacity at the desired cycle volume, sensor 130 generates a signal that is received by control unit 138. Control unit 138 in accordance with a pre-selected conditions) or input signal(s) effects the cycle switch by controlling valve 140 introducing a gas into (and pressurizing) chamber 142 forcing out fluid from body fluid chamber 137. Additionally control unit 138 generates one or more signals or an electrical current to control valves 114 and 116, i.e., to close valve 114 and open valve 116, to effect downstream flow of the body fluid into the treatment unit 112.

Controller 138 receives one or more input signals from a sensor device in the treatment system 100. In a preferred embodiment, controller then compares the signals (or employs a comparator) to one or more pre-selected conditions optimally contained within a lookup table stored in a memory device, and in response, generates one or more output signals to control one or more valves. In one embodiment, during the vacuum portion of flow cycle for pumping chamber 102, controller 138 receives a first signal from sensor 130 indicative of a change in fluid flow rate. In response, controller compares the first signal with a first value in the lookup table corresponding to a pre-selected flow rate change. If the first signal is greater that the first value, then controller generates one or more output signals to valves 114, 116 and 140 to effect control of these valves and initiate the next flow cycle sequence such as the pressurization portion and consequently induce expulsion of fluid from body fluid chamber 137 into flow circuit 101 in the direction indicated by arrow 105.

The pre-selected conditions can be selected to be indicative of any desired fluid flow or change in fluid flow. Preferably in one embodiment, the pre-selected flow rate change is selected to be at least about a 10% decrease in fluid flow, more preferable at least about a 20% decrease, and still more preferably at least about 25% decrease measured in ml per minute by considering the highest fluid flow rate detected during a selected portion of the pumping cycle, for example, during the pressurization portion or the vacuum portion of an individual pumping cycle.

In other embodiments a pre-selected flow rate is selected to be less than or equal to a desired flow rate. In selected embodiments, the desired flow rate is selected to be less than about 10 ml per minute, more preferably less than or equal to about 5 ml per minute, and still more preferable less than or equal to about 3 ml per minute.

In the illustrated embodiment, a vacuum/pressure source 151 supplying both vacuum pressure and positive pressure are both provided by pump 148 and controlled through valves 150, 152, and 140 as well as vacuum pressure regulator 154. and positive pressure regulator 156. Other optional features include, but are not limited to, pressure transducer, line filters, as for example, but without limitation, biohazard filter; temperature sensors and heaters, in-line pressure sensors and alarms, and the like.

A second vacuum/pressure source 160 provided as previously described for vacuum/pressure source 151, second pumping chamber 104 and associated valves 118, 120, and 162 can be similarly controlled. Alternatively, the vacuum source 160 can be the same source and/or apparatus used for first pumping chamber 102 or it can be a separate source and/or apparatus. Control unit 138 can provide an output signal to one or more of valves 118, 120 and 162 effect these valves to close or open according to a desired sequence.

Alternatively, second pump chamber 104 and the associated valves 118 120, and 162 can be controlled to be 180° out of phase during the pumping cycle for pumping chamber 102. In this aspect, second pump chamber and the associated valves are controlled such that body fluid is drawn into body fluid chamber 163, while at the same time upstream at pumping chamber 102 body fluid is being expelled from body fluid chamber 136.

Further, second pump chamber 104 and the associated valves 118 120, and 162 can be controlled to be to expel body fluid from body fluid chamber 163 at any time either with the substantially the same cycle time period as pump chamber 102 or with any other cycle time period as desired.

In selected applications a second pumping chamber provides particular advantages controlling the fluid flow rate in the fluid treatment unit 112. One advantage is the supply of a substantially continuous flow rate supplied to a flow circuit or treatment system. In other examples where the treatment includes a fluid permeable membrane such as used in plasmafiltration and/or hemofiltration treatments, second pumping chamber 104 can be utilized in conjunction with first pumping chamber 102 to control the transmembrane fluid flow rate. Fluid flow from the body fluid side of a permeable membrane to the dialysate or sorbent side 103 of the membrane in the treatment unit may be increased by any one of four methods: 1) exerting positive pressure from first pumping chamber 102 while valves 114 and 118 are closed and valve 116 is open; 2) exerting positive pressure from second pumping chamber 104 while valves 120 and 116 are closed and valve 118 is open: 3) exerting positive pressure from both pumping chambers 102 and 104 while valves 114 and 120 arc closed and valves 116 and 118 are open; and 4) exerting vacuum pressure on the sorbent/dialysate side 103 of the membrane to pull fluid through the membrane.

By proper coordination of first and second pumping chambers 102 and 104. together with flow control valves 114, 116, 118, 120, the net fluid movement across a permeable membrane in treatment unit 112 can be precisely controlled. In addition, the efficiency of filtration or dialysis may be greatly enhanced by alternatingly driving fluid back and forth across the permeable membrane in treatment unit 112 hereby increasing exchange with any dialysate and increasing body fluid fraction contact with any sorbent for toxin removal, etc.

The positioning of the pumping chamber along the body fluid flow circuit depends on the treatment being conducted. For most treatments involving dialysis or filtration, it is preferred to couple the pumping chamber to the body fluid inflow line, upstream from the treatment unit. For other applications wherein the treatment does not involve partial fluid transfer across a membrane, pumping chamber can be couple to either the body fluid inflow line or outflow line, as desired within other design considerations. Example of such therapies include, without limitation, blood irradiation therapy, phototherapies including photo activation of pharmaceuticals in circulation in the body fluid being treated.

In another embodiment of the present invention particularly suited to applications wherein the treatment unit is a filtration treatment, as for example, but not limited to hemofiltration or plasmafiltration, a first pumping chamber is coupled to and in fluid communication with the body fluid inflow line as described above, and a second pumping chamber is couple to and in fluid communication with the body fluid outflow line. One or more flow control valves are coupled to and in fluid communication with the body fluid outflow line so as to coordinate the second pumping chamber to control body fluid flow from the treatment unit and back to the patient through the patient access. As an alternative to a second pumping chamber, alternative types of pumps can be used including, for example, and without limitation, a roller pump.

Though systems can be designed to pump widely varying volumes of body fluid per cycle of vacuum and positive pressure, preferred volumes are equal to a significant proportion of the fluid volume of the body fluid treatment unit, as for example, but without limitation, about 20-50% of the fluid volume of the treatment unit. Likewise, for systems using a single lumen patient access, it is preferred that the cycle volume of body fluid be relatively large in relation to the volume of the catheter to avoid over cycling that portion of the treated body fluid returned to the catheter for re-infusion into the patient that remains in the catheter at the start of a new cycle of vacuum draw of body fluid. By way of example, but without limitation, in a blood treatment protocol, a preferred cycle volume should be at least about 10-15 times the volume of the catheter. In one preferred embodiment, the cycle volume is between about 30-60 ml, more preferably between about 40-50 ml of body fluid.

As with cycle volumes, cycle times for one cycle of alternating through vacuum and positive pressure may vary widely to suit various applications of the present invention. Cycle times are determined based on the cross-sectional area of the patient access and How lines, the vacuum and positive pressures used, and the resistance to flow exerted by the device and the patient's body. Typical cycle times for a blood treatment protocol range between about 3 seconds to about 30 seconds for one full cycle of vacuum and positive pressure. Preferably the maximum suitable cycle time for a given system is selected to be sufficiently a short time period to avoid adverse effects from stagnation of the volume of fluid in the treatment unit during the vacuum (fill) portion of the cycle, such as settling, coagulation and adhesion of proteins, etc. to surfaces within the treatment unit.

Figure 8:
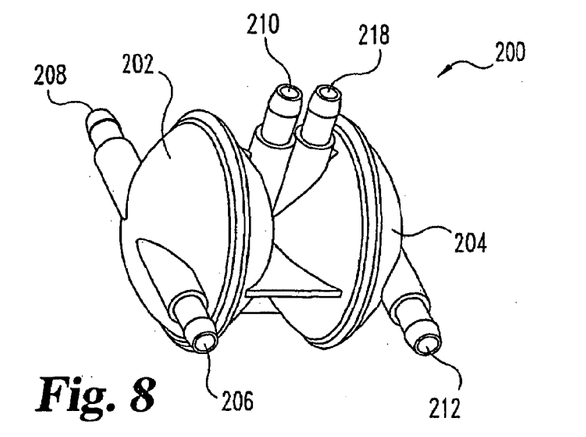
FIG. 8 is a perspective view of one embodiment of a dual chamber pump provided according to the present invention.
Figure 9:
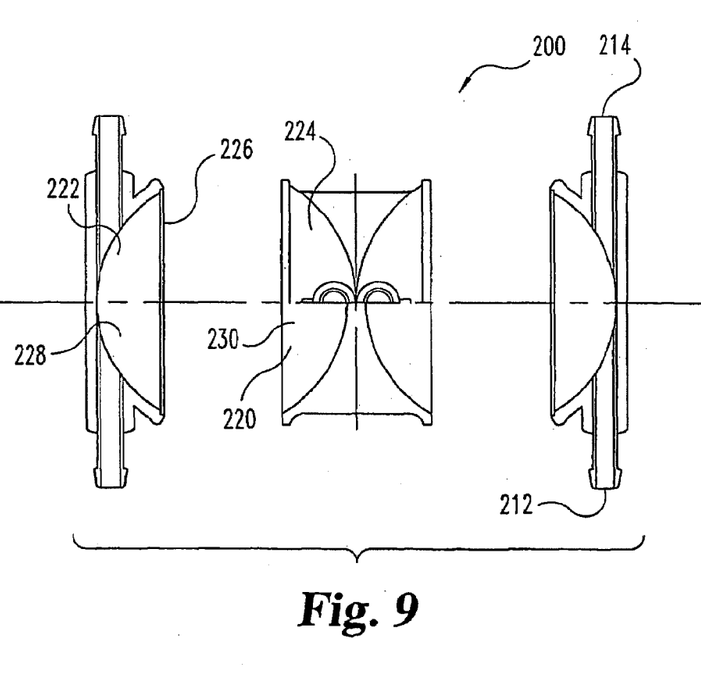
FIG. 9 is an exploded view side elevation view in partial section of the dual chamber pump illustrated in FIG. 8.

FIGS. 8 and 9 illustrate one embodiment of a dual chamber pump 200 provided according to this invention. Pump 200 includes a first pumping chamber 202 adjacent to a second pumping chamber 204. First pumping chamber 202 includes first fluid port 206, an opposite second fluid port 208 and a gas port 210. Second pumping chamber 204 mirrors first pumping chamber 202. Consequently second pumping chamber includes a pair of fluid ports 212 and 214 and a gas port 218.

Referring specifically to FIG. 9. the exploded view of dual chamber pump 200 reveals an interior cavity 220 defined by the pair of claim shell shaped halves 222 and 224. In one embodiment flexible membrane 226 is positioned between halves 222 and 224 and defines an inner chamber 228 and an outer chamber 230. In alternative embodiments flexible member is provided or configured as an expandable bag nested inside interior cavity 220.

In one embodiment, the flexible membrane 226 is readily replaced and can be provided as a disposable membrane or diaphragm. Membrane 226 can be formed of an elastomeric material with or without resistance to elongation or deformation. In one embodiment the elastomeric material does not exhibit an elastic memory to resist deformation during the vacuum portion of a pumping cycle. In other embodiments the membrane does exhibit an elastic memory. Membrane 226 can be formed of a wide variety of polymeric materials that are biocompatible, capable of being sterilized, and impermeable to body fluid. Examples of polymeric materials useful in the present invention include, but are not limited to: polyesters, polyamides, polyolefins, polysulfones, polyvinyl chloride, silicone rubbers, polyurethanes, polypropylene, polyethylene and the like.

Prior to use or after use one or both of pumping chambers can be opened as depicted in FIG. 9 and the flexible membrane 226 replaced. The two halves 222 and 224 can be releasably secured together by methods and devices known in the art, for example, the halves 222 and 224 can be secured with a removable locking ring, snap ring, exterior clamp, bolts, interlocking tabs and the like. Before use either prior to recombining halves 222 and 224 sandwiching membrane 226 there between or subsequent thereto dual pumping chamber 200 is sterilized for use in one or more fluid flow circuits described herein.

The pumping chamber is preferably configured to draw a steady, preset vacuum pressure when desired of between about −150 and about −400 mm/Hg. more preferably between about −200 and about −300 mm/Hg. For most applications wherein the body fluid being treated is blood, a vacuum pressure of about −250 mm/Hg will be most preferred to maximize How and minimize the risk of venous collapse is significantly less when the blood is being drawn under vacuum pressures no lower than −250 mm/Hg. though there is naturally great variability in the vacuum pressure individual veins are able to tolerate. Greater vacuum pressures may be tolerable in some individuals, though risks of venous collapse are high. Lesser vacuum pressures may also be used, but they tend to produce relatively low body fluid flow rates, thereby requiring relatively long treatment sessions, which may not be desirable or practical in many clinical sellings.

Likewise, the pumping chamber is preferably configured to exert a steady, preset positive pressure to expel body fluid in the pumping chamber when desired at a pressure of between about +150 and about +400 mm/Hg. more preferably between about +200 and about +300 mm/Hg. The magnitude of positive pressure is not as critical as the vacuum pressure in that most body fluids can tolerate greater pressures exerted on them through the treatment unit, where tissue collapse or other damage is not a major concern. Furthermore, re-infusion pressures after treatment can be regulated downstream of the treatment unit, before reentry into the patient. It is often convenient to operate the pumping chamber at positive pressures of the same magnitude as the vacuum pressure asserted, as for example, without limitation at about +250 mm/Hg. particularly when the fluid being treated is blood. Other considerations, such as the rate of fluid transfer across permeable membranes in the treatment unit may indicate preferences for other positive pressure settings.

Figure 10:
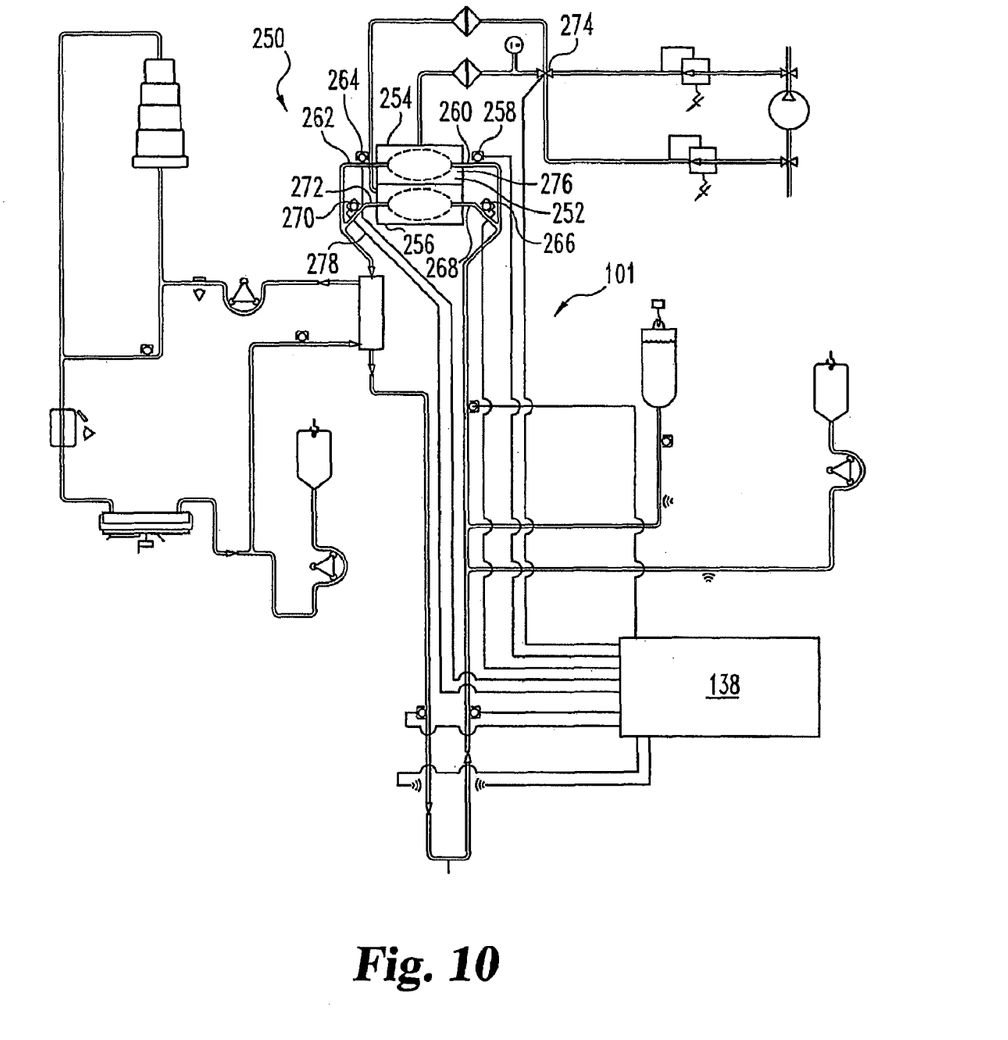
FIG. 10 is a schematic illustrating use of the dual chamber pump illustrated in FIG. 8 in a body fluid treatment system.
Figure 11:
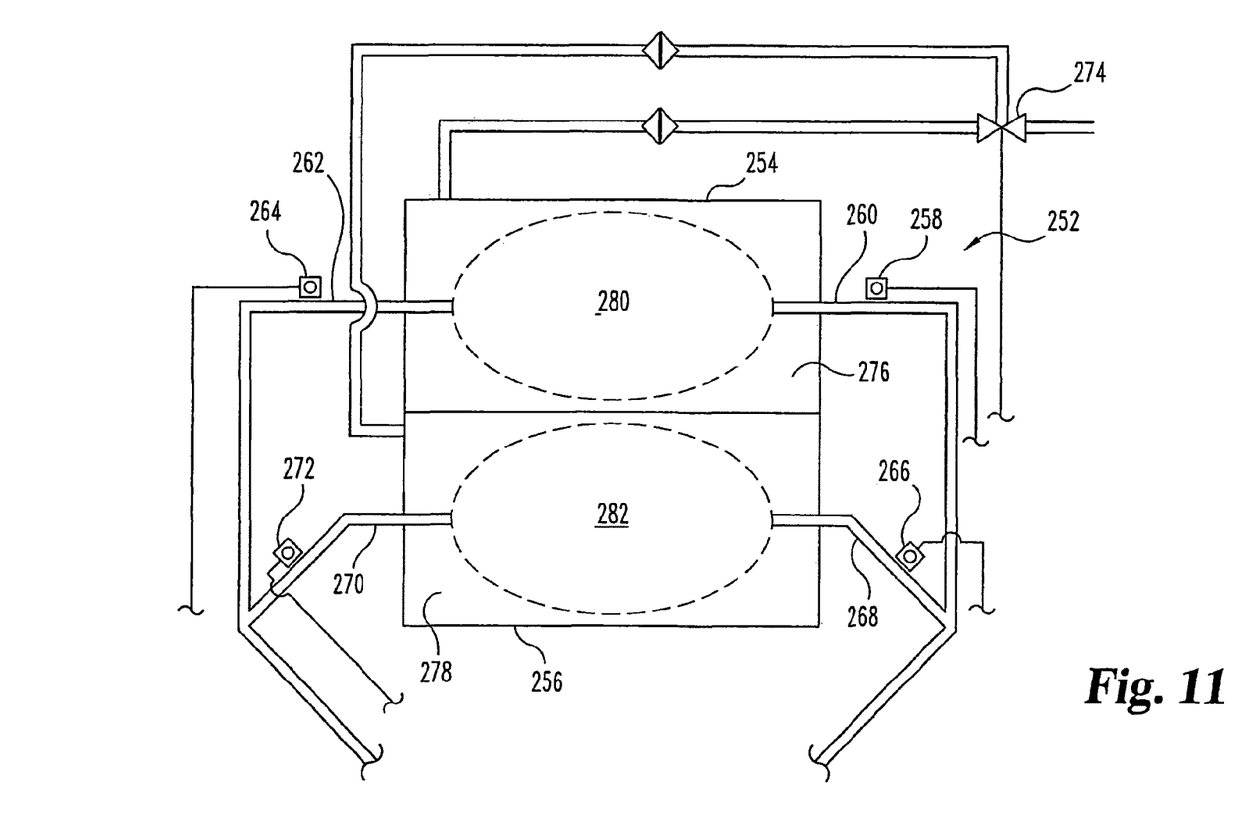
FIG. 11 is an enlarged view of the dual chamber pump in the body fluid treatment system of FIG. 10.

FIG. 10 is a schematic illustration of another embodiment of a body treatment system 250 presided according to the present invention. FIG. 11 is an enlarged view illustrating the dual chamber pump 252 in system 250. System 250 is configured similar to system 200 illustrated in FIG. 7 with the exception that a dual chamber pump replaces the first and second pumping chambers 102 and 104. Like components between the two systems are designated with the same reference numbers.

System 250 includes a dual pumping chamber 252. Dual pumping chamber 252 can be, but is not limned to, the dual pumping chamber provided as illustrated in FIGS. 8 and 9. Pumping chamber 252 includes a first body fluid pump 254 and a second body fluid pump 256 first pump 254 includes a first valve 258, inlet port 260, exit port 262 and second valve 264. Similarly, second pump 256 includes a third valve 266, inlet port 268, exit port 270 and fourth valve 272. In use dual pumping chamber 252 can operate in a parallel mode, a dual capacity mode or in series.

In a parallel mode of operation the two pumping chambers 254 and 256 alternatively withdraw and expel body fluid approximately 180° out of sync with respect to each other. That is, while pumping chamber 254 is operating in the vacuum (filling) portion of a pumping cycle pumping chamber 256 is operating in the pressurized (expelling) portion of the pumping cycle. In this mode, valve 274 switches to evacuate gas chamber 276 and pressurizes gas chamber 278, while valves 258 and 272 are open, and valves 266 and 264 are closed.

In a dual capacity of mode, both pumping chambers 254 and 256 are operating in the same portion of the pumping cycle. That is, while pumping chamber 254 is operating in the vacuum portion of the pumping cycle and aspirating body fluid into an inner chamber, pumping chamber is similarly operating on substantially same pumping cycle and also aspirating body fluid into an inner chamber, fn this mode, valve 274 switches to evacuate both gas chambers 276 and 278, while valves 276 and 266 are opened and valves 264 and 272 are closed. After the body fluid chambers 280 and 282 are filled with the desired amount of fluid, valve 274 switches to pressurize chambers 276 and 278, while valves 276 and 266 are closed and valves 264 and 272 are opened. The result is that a bolus equal to approximately twice the volume of each individual chamber is forced through a flow circuit with each pumping cycle.

In yet another embodiment, the dual pumping chamber can operate in series. This mode of operation is similar to the mode depicted in FIG. 7 where first and second pumping chambers are positioned in different regions of the flow circuit. In this mode of operation body fluid is first pumped through first chamber 254 and forced into flow circuit 101 and thereafter at least a portion of the body fluid is pumped through pumping chamber 256. The two pumping chamber can, but are not required to be operating approximately 180° degrees out of phase.

While these mode of operation have been described by referring to either in sync or 180° out of phase considering the timing of the pumping cycle, it should be understood that the pumps can be operating independently of each other or their pumping cycles coordinated with each other but out of phase by 0° to about 180°.

In another aspect of the present invention, a method is provided for controlling the body fluid flow from a patient through a body fluid flow circuit, through a body fluid treatment unit, and back to the patient. In one form of the invention, a method comprises alternating drawing the body fluid into the body fluid flow circuit under a predetermined vacuum pressure and pushing the drawn body fluid through the circuit under a predetermined positive pressure. By pumping the cycle volume of body fluid from the body under a steady vacuum pressure, rather than at a certain volume rate, as for example, dictated by a certain roller pump rate, which is designed to pump a specific volume of fluid per unit time, regardless of the pressures exerted by the pump to achieve that flow rate, excessive vacuum pressures are not generated which cause venous collapse around the patient access. This allows the device to operate at an optimized rate fitted to the patients individual How rate limitations without complicated monitoring by trained attendants.

In one embodiment of this aspect of the invention, the alternating vacuum and positive pressures are exerted on a pumping chamber such that the chamber fills with blood or other body fluid to be treated, drawn from the patient under an applied vacuum pressure, and the chamber empties of the body fluid under said exerted positive pressure. An appropriate flow control valve or valves are coordinated as described above, with said alternating pressures to effect a net downstream blood flow through the blood flow circuit.

In another inventive method, the flow control valves are coordinated as described above to allow a percentage of the body fluid in the treatment unit to back-flush out of the treatment unit to wash treatment unit surfaces and maintain mixing of the body fluid. Such back flushing can also be used to alternately drive fluid back and forth across permeable membranes in the treatment unit, if any, as for example, but without limitation, when the treatment unit is a dialyzer or filtration unit.

It should also be understood that while specific features, components, systems and methods of operation have been discussed herein in relation to a specific embodiment, each of the features, components systems and modes of operation can be used conjunction with any of the described other embodiments and/or methods.

Though the devices and methods of the present invention are best suited for use in the treatment of a patients body fluids as drawn directly from and returned directly to the patient, the invention may also be readily adapted for treating body fluids or fractions thereof remote from a patient, including but not limited to blood fractions and blood bank pools of blood fractions.

While the invention and its preferred embodiments have been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected as set forth in the following claims.

What is claimed is:

1. A body fluid treatment apparatus comprising:
a body fluid pumping chamber containing a flexible membrane that is configured to draw body fluid into the pumping chamber under negative gaseous pressure on a gas side of the membrane and alternately to expel body fluid from the pumping chamber under positive gaseous pressure on the gas side of the membrane;
a sensor that is configured to provide a flow rate signal representing the flow rate of body fluid flowing into the pumping chamber; and
a control apparatus that is configured to pressurize the pumping chamber on the gas side of the membrane alternately with positive and negative gaseous pressure with reference to the flow rate signal by a) pressurizing the gas side with negative gaseous pressure and b) switching the gaseous pressure at the gas side from negative to positive upon determining that the flow rate into the pumping chamber has decreased in an amount that is predetermined to result from greater flow resistance as the pumping chamber reaches capacity at a desired cycle volume.

2. An apparatus as defined in claim 1 further comprising a dialyzer and a blood flow circuit, wherein the blood flow circuit is configured to convey blood from a patient to the pumping chamber under the influence of the negative gaseous pressure at the pumping chamber, and to convey blood from the pumping chamber through the dialyzer and back to the patient under the influence of the positive gaseous pressure at the pumping chamber.

3. An apparatus as defined in claim 1 wherein the pumping chamber is one of two body fluid pumping chambers, each of which contains a flexible membrane that is configured to draw body fluid into the respective pumping chamber under negative gaseous pressure on a gas side of the membrane and alternately to expel body fluid from the respective pumping chamber under positive gaseous pressure on the gas side of the membrane; and wherein the control apparatus is configured to pressurize the two pumping chambers alternately with positive and negative gaseous pressure on the gas sides of the membranes to move body fluid through the two pumping chambers in a coordinated relationship.

4. An apparatus as defined in claim 3 wherein the coordinated relationship is in phase.

5. An apparatus as defined in claim 3 wherein the coordinated relationship is out of phase.

6. An apparatus as defined in claim 5 wherein the coordinated relationship is out of phase by about 180 degrees.

7. An apparatus as defined in claim 3 wherein the two pumping chambers are in parallel.

8. An apparatus as defined in claim 3 wherein the two pumping chambers are in series.

9. An apparatus as defined in claim 3 further comprising a dialyzer and a blood flow circuit, wherein the blood flow circuit is configured to convey blood from a patient to the pumping chambers under the influence of the negative gaseous pressure at the pumping chambers, and to convey blood from the pumping chambers through the dialyzer and back to the patient under the influence of the positive gaseous pressure at the pumping chambers.

* * * * *

UNITED STATES PATENT AND TRADEMARK OFFICE
CERTIFICATE OF CORRECTION

| | | |
|---|---|---|
| PATENT NO. | : 7,998,101 B2 | Page 1 of 1 |
| APPLICATION NO. | : 11/860026 | |
| DATED | : August 16, 2011 | |
| INVENTOR(S) | : Stephen R. Ash | |

It is certified that error appears in the above-identified patent and that said Letters Patent is hereby corrected as shown below:

Title Page Column 1 (Title), line 3:
    delete "TREATMENT" and replace with --TREATMENTS--.

Title Page Column 2 (Abstract), line 3:
    delete "60" and replace with --60,--.

Column 1, line 3:
    delete "TREATMENT" and replace with --TREATMENTS--.

Signed and Sealed this
First Day of May, 2012

David J. Kappos
*Director of the United States Patent and Trademark Office*